US008818070B2

(12) United States Patent
Hong et al.

(10) Patent No.: US 8,818,070 B2
(45) Date of Patent: Aug. 26, 2014

(54) PREDICTING TOXICITY OF A COMPOUND OVER A RANGE OF CONCENTRATIONS

(75) Inventors: Suk Jin Hong, Roscoe, IL (US); Richik Niloy Ghosh, Upper St. Clair, PA (US)

(73) Assignee: Cellomics, Inc., Pittsburgh, PA (US)

( * ) Notice: Subject to any disclaimer, the term of this patent is extended or adjusted under 35 U.S.C. 154(b) by 239 days.

(21) Appl. No.: 13/402,219

(22) Filed: Feb. 22, 2012

(65) Prior Publication Data

US 2012/0219204 A1 Aug. 30, 2012

Related U.S. Application Data

(60) Provisional application No. 61/447,423, filed on Feb. 28, 2011.

(51) Int. Cl.
*G06K 9/00* (2006.01)

(52) U.S. Cl.
CPC ................................. *G06K 9/00127* (2013.01)
USPC .............................................. 382/133; 435/4

(58) Field of Classification Search
None
See application file for complete search history.

(56) References Cited

U.S. PATENT DOCUMENTS

| 7,817,840 | B2 * | 10/2010 | Mattheakis et al. | 382/133 |
| 8,515,150 | B2 * | 8/2013 | Mangoubi et al. | 382/133 |
| 2006/0234332 | A1 * | 10/2006 | Mattheakis et al. | 435/40.5 |
| 2007/0015210 | A1 * | 1/2007 | Ezekiel | 435/7.1 |
| 2007/0202487 | A1 * | 8/2007 | Fan | 435/4 |
| 2007/0250301 | A1 * | 10/2007 | Vaisberg et al. | 703/11 |
| 2009/0170091 | A1 * | 7/2009 | Giuliano et al. | 435/6 |

FOREIGN PATENT DOCUMENTS

| GB | 2 435 925 | 9/2007 |
| WO | WO 2009/002565 | 12/2008 |

OTHER PUBLICATIONS

Abraham et al., *Application of a High-Content Multiparameter Cytotoxicity Assay to Prioritize Compounds Based on Toxicity Potential in Humans*, J. Biomol Screen 2008, vol. 13, pp. 527-537.
O'Brien et al., *High Concordance of Drug-Induced Human Hepatotoxicity with in Vitro Cytotoxicity Measured in a Novel Cell-Based Model Using High Content Screening*, Arch. Toxicol., vol. 80, 2006, pp. 580-604.
Xu et al., *Cellular Imaging Predictions of Clinical Drug-Induce Liver Injury*, Toxicological Sciences, 105(1), 2008, pp. 97-105.
International Search Report issued May 10, 2012, in related Application No. PCT/US2012/026079, filed Feb. 22, 2012.

\* cited by examiner

*Primary Examiner* — Jason M Repko
*Assistant Examiner* — Shervin Nakhjavan
(74) *Attorney, Agent, or Firm* — Workman Nydegger

(57) ABSTRACT

A method of predicting hepatotoxicity of a compound. The method includes imaging cells of hepatic origin positioned within a plurality of containers to obtain imaged cellular targets, each container being treated with a different concentration of the compound, the imaging being performed using a quantitative high-content cell imaging system; quantitatively measuring the imaged cellular targets to detect changes in multiple cellular targets associated with cytotoxicity of the compound; and analyzing measurements obtained from the measured imaged cellular targets over a range of compound concentrations to determine the hepatotoxicity of the compound.

14 Claims, 11 Drawing Sheets

| Conc. (1x) | Drug1 | | | Drug2 | | | Negative Drug | | | Control (Vehicle) | | |
|---|---|---|---|---|---|---|---|---|---|---|---|---|
| 0.75 Cmax | A1 | A2 | A3 | A4 | A5 | A6 | A7 | A8 | A9 | A10 | A11 | A12 |
| 1.56 Cmax | B1 | | | B4 | | | B7 | | | B10 | | |
| 3.13 Cmax | C1 | | | C4 | | | C7 | | | C10 | | |
| 6.25 Cmax | D1 | | | D4 | | | D7 | | | D10 | Ref | |
| 12.5 Cmax | E1 | | | E4 | | | E7 | | | E10 | | |
| 25 Cmax | F1 | | | F4 | | | F7 | | | F10 | | |
| 50 Cmax | G1 | | | G4 | | | G7 | | | G10 | | |
| 100 Cmax | H1 | | | H4 | | | H7 | H8 | H9 | H10 | | |

| Drug Name | Cell Loss | DNA | GSH | ROS | Mito | # of targets flagged as being toxic | Hepato-toxicity Prediction |
|---|---|---|---|---|---|---|---|
| FCCP | + | + | + | + | - | 4 | P |
| Mefenamic Acid | + | + | + | - | + | 4 | P |
| Gemfibrozil | + | + | + | + | + | 5 | P |
| Nalidixic Acid | - | + | - | + | - | 2 | P |
| Hycanthone | + | + | + | + | + | 5 | P |
| Tetracycline | + | + | + | + | + | 5 | P |
| Ticlopidine | + | + | + | + | + | 5 | P |
| Trazodone HCl | + | + | + | - | + | 4 | P |
| Phenylbutazone | + | + | + | + | - | 4 | P |
| Cyproheptadine HCl | + | + | + | + | + | 5 | P |
| Dantrolene Sodium | + | + | + | + | - | 4 | P |
| Novobiocin | + | + | + | + | + | 5 | P |
| Troglitazone | + | + | + | - | + | 4 | P |
| Rosiglitazone | - | - | - | - | - | 0 | N |
| Aspirin | - | - | - | - | - | 0 | N |
| Fluoxetine | - | - | - | - | - | 0 | N |
| Melatonin | - | - | - | - | - | 0 | N |
| Multiplier (K) calculated for threshold | 3 | 2 | 3 | 2 | 3 | P: positive N: negative | |

PREDICTING TOXICITY OF A COMPOUND OVER A RANGE OF CONCENTRATIONS

CROSS REFERENCES TO RELATED APPLICATIONS

This application claims priority to U.S. Provisional Patent Application No. 61/447,423, filed on Feb. 28, 2011, the contents of which are hereby incorporated by reference.

BACKGROUND OF THE INVENTION

1. The Field of the Invention

The present invention relates to assay methods to predict compound toxicity.

2. The Relevant Technology

A major reason for drugs to be withdrawn from the market after the drugs have been launched is because they may cause liver injury. The trend in drug discovery is efficient compound attrition where a compound's toxicity is identified as early as possible in the drug discovery process and thus the compound can be removed from further development. Due to regulatory, ethical and cost issues, the use of animal testing to identify potential hepatotoxic compounds early in the drug discovery process is often not feasible. The challenge is to identify an affordable in vitro assay method that can be used early in the drug discovery process and that can predict whether a compound is hepatotoxic with high specificity and sensitivity. Although there exists various methods to detect the potential hepatotoxicity of a drug compound, most perform poorly in predicting hepatotoxicity of the compound of interest.

Good predictivity for toxicity requires an assay which determines whether a compound is toxic with high specificity (i.e., a low percentage of false positives) and high sensitivity (i.e., a low percentage of false negatives). Previously, O'Brien et al. (Arch. Toxicol., 2006, 80:580-604) showed that the simultaneous measurement of multiple cell health indicators in hepatic cells using an automated quantitative imaging-based detection method (i.e., high content imaging) predicted drug hepatotoxicity with high sensitivity and specificity. A more recent study by Xu et al. (Toxicological Sciences, 2008, 105(1):97-105) using a similar high-content imaging approach but directed towards different cellular targets also showed that a high-content, quantitative, cell-imaging based assay on hepatic cells can predict the hepatotoxicity of compounds. Although the above-cited methods have been used to predict the potential hepatotoxicity of compounds with good sensitivity and specificity, the lack of convenience, robustness and ease of use of these assay methods have hindered their adoption as assays to be routinely performed for compound hepatotoxicity detection.

A challenge in determining compound toxicity is that different cellular targets exhibit toxic responses at different doses for different compounds. For example, in a condition called hormesis, a compound may show its toxicity at an intermediate concentration but not at a higher concentration. Previous work in the art has not dealt with this issue, as conventional methods either monitor toxicity at a specific compound dose (e.g., Xu et al.) or use a compound's $EC_{50}/IC_{50}$ concentration to assess toxicity (e.g., O'Brien et al.). However, many cellular targets do not exhibit a classic sigmoidal dose-response curve with many compounds and may also exhibit hormesis-like effects, making it difficult to determine the $EC_{50}/IC_{50}$ concentration of the compounds for a specific target. A method to robustly deal with the variations in specific target response and to accurately assess compound toxicity by monitoring a range of concentrations would improve the predictivity of toxicity assays.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope. In the drawings, like parts are given like reference numerals.

FIG. 9 is a spreadsheet illustrating test results of hepatotoxicity predictions of various compounds using rat primary hepatocytes;

DETAILED DESCRIPTION OF THE PREFERRED EMBODIMENTS

As used in the specification and appended claims, directional terms, such as "top," "bottom," "up," "down," "upper," "lower," "proximal," "distal," and the like are used herein solely to indicate relative directions and are not otherwise intended to limit the scope of the invention or claims.

Embodiments of the present invention are directed to robust hepatotoxicity prediction assay methods with innovations that provide a highly predictive in vitro assay for hepatotoxicity and are easy to implement and use. In one embodiment, the assay methods use cells of hepatic origin, a quantitative high-content cell imaging system (e.g., ToxInsight™, CellInsight™, or ArrayScan® instrument platforms manufactured by Cellomics Inc., a subsidiary of Thermo Fisher Scientific Inc. or other high-content cell imager), fluorescent reagents to label specific cell-health associated cellular targets, an optimized assay protocol, and a decision-making analysis to predict compound toxicity using the quantitative data from the cell images. The optimized reagents, experimental workflow, and decision-making software make this an easier and more robust hepatotoxicity assay to implement and use than conventional methods.

Although the embodiments discussed herein are directed to assess whether compounds are hepatotoxic, other types of cell toxicity can also be determined using the processes disclosed herein in conjunction with non-hepatic cells. For example, cancer cells can be used to investigate cancer cell toxicity, cardiac cells can be used to investigate cardiotoxicity, dermal cells can be used to investigate dermal toxicity, neuronal cells can be used to investigate neurotoxicity, and normal cells can be used to investigate cytotoxicity. Other types of cell toxicity can also be determined.

Figure 1:
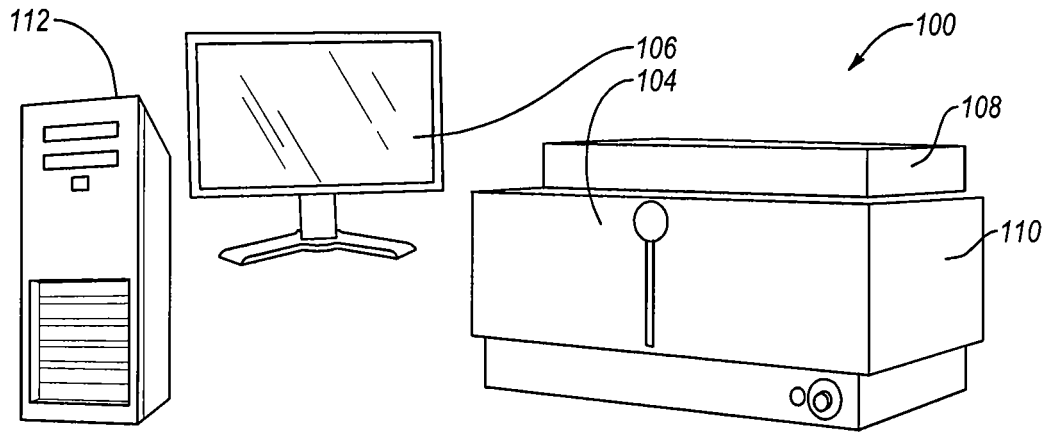
FIG. 1 is a front perspective view of an exemplary system incorporating features of the present invention.

FIG. 1 is a block diagram illustrating an exemplary system 100 incorporating features of the present invention. At the heart of system is a quantitative high-content cell imaging system 102 in which cells are scanned and analyzed. The exemplary imaging system 102 includes, but is not limited to, an imaging device 104 with a user display device 106. Imaging device 104 generally includes a stage housing 108 mounted on a microscope assembly 110 having a plurality of objectives. Stage housing 108 is configured to house the components required to position a specimen plate (such as, e.g., 96-well plate 126 shown in FIG. 3) containing cells so microscope assembly 110 can image the cells using the objectives to allow high content screening of the cells to be performed, as is known by one skilled in the art. Analyzing and storing of the data obtained from the imaging can be performed by imaging device 104 with results being displayed to the user on user display device 106.

System 100 can also include an external computing device 112, if desired. External computing device 112 can comprise a general purpose or specialized computer or server or the like. External computing device 112 can be used as a controller for the system as well as for performing, by itself or in conjunction with imaging device 104, the analyzing and/or storing of the data obtained by imaging device 104. In some embodiments, external computing device 112 can also display results to the user on user display device 106. External computing device 112 can communicate with imaging device 104 and/or display device 106 directly or through a network, as is known in the art.

In one embodiment of the invention, one or more of the method steps described herein are performed as a software application. However, the present invention is not limited to this embodiment and the method steps can also be performed in firmware, hardware or a combination of firmware, hardware and/or software. Furthermore, the steps of the application can exist solely on imaging device 104, solely on external computing device 112, or on a combination of both.

An operating environment for the devices of the system may comprise or utilize a processing system having one or more microprocessors and system memory. In accordance with the practices of persons skilled in the art of computer programming, the present invention is described below with reference to acts and symbolic representations of operations or instructions that are performed by the processing system, unless indicated otherwise. Such acts and operations or instructions are referred to as being "computer-executed," "CPU-executed," or "processor-executed."

The processing system may also include physical storage media and other computer-readable media for storing computer-executable instructions and/or data structures which are used by the one or more computing microprocessors. Such computer-readable media can be any available media that can be accessed by a general purpose or special purpose computer. Computer-readable media that store computer-executable instructions are physical storage media. Computer-readable media that carry computer-executable instructions are transmission media. Thus, by way of example, and not limitation, embodiments of the present invention may comprise at least two distinctly different kinds of computer-readable media: physical storage media and transmission media.

Physical storage media used in embodiments of the present invention may include magnetic disks, optical disks, organic memory, RAM, ROM, EEPROM, flash memory, or any other medium which can be used to store desired program code means (i.e., software) in the form of computer-executable instructions or data structures and which can be accessed by the one or more microprocessors to implement aspects of the invention, such that they are not merely transitory carrier waves or propagating signals.

Computer-executable instructions comprise, for example, instructions and data which, when executed by one or more microprocessors, cause a general purpose computer, special purpose computer, or special purpose processing device to perform a certain function or group of functions, including the functions described herein, as aspects of the invention. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Figure 2:
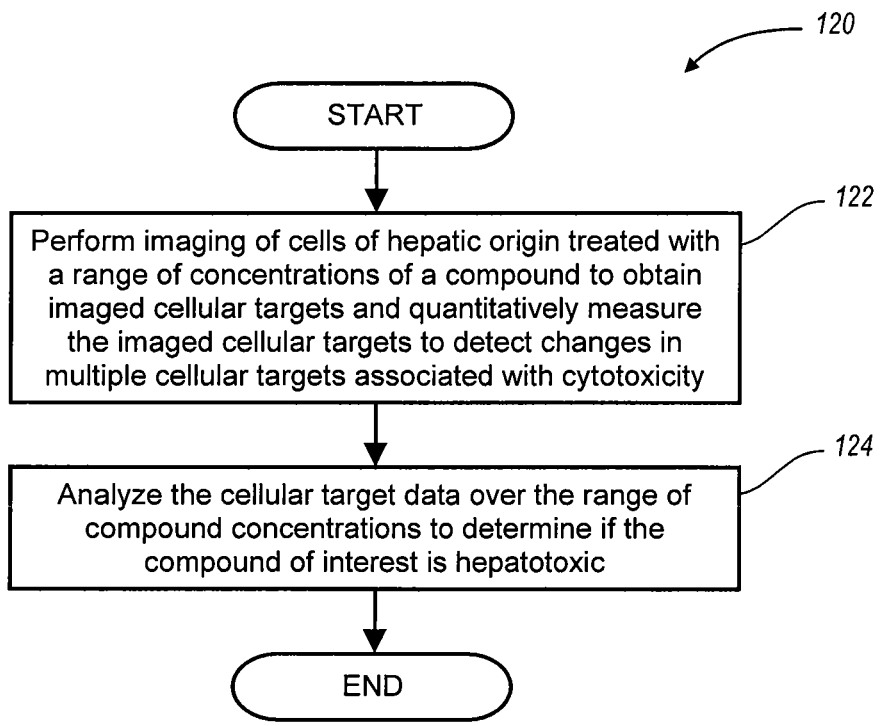
FIG. 2 is a flow diagram illustrating a method for determining hepatotoxicity of a compound.

FIG. 2 is a flow diagram illustrating an assay method 120 for determining the hepatotoxicity of a compound according to one embodiment. The first part of the exemplary process, denoted as step 122, includes a specific manner of treatment and fluorescent labeling of cells of hepatic origin. Specifically, in step 122, imaging of cells of hepatic origin treated with a range of concentrations of a compound is performed to obtain imaged cellular targets and the imaged cellular targets are quantitatively measured to detect changes in multiple cellular targets associated with cytotoxicity.

In many of the examples discussed herein, the cellular targets and cell properties monitored in the assays are cell loss, cellular redox stress and the mitochondrial stress in the cell; however, other cellular properties, functions or targets (collectively referred to herein as "targets") can also be monitored following the process to assess cell health, as discussed in more detail below.

The second part of the exemplary process, denoted as step 124, uses the quantitative multiparametric cellular target data acquired in step 122 and analyzes the data over the range of compound concentrations to determine if the compound of interest is hepatotoxic. This exemplary hepatotoxicity detection and analysis process 120 enables the systematic investigation of toxic events in hepatic cells more robustly than existing methods, and accurately predicts the hepatotoxicity of compounds with high specificity and sensitivity (i.e., low false positive and negative rates respectively). The exemplary process 120 assesses compound toxicity over a range of compound concentrations and robustly deals with non-unidirectional responses of the monitored cellular properties (e.g., hormesis), thus providing more robust predictions of compound toxicity than existing methods.

Figures 3, 4:
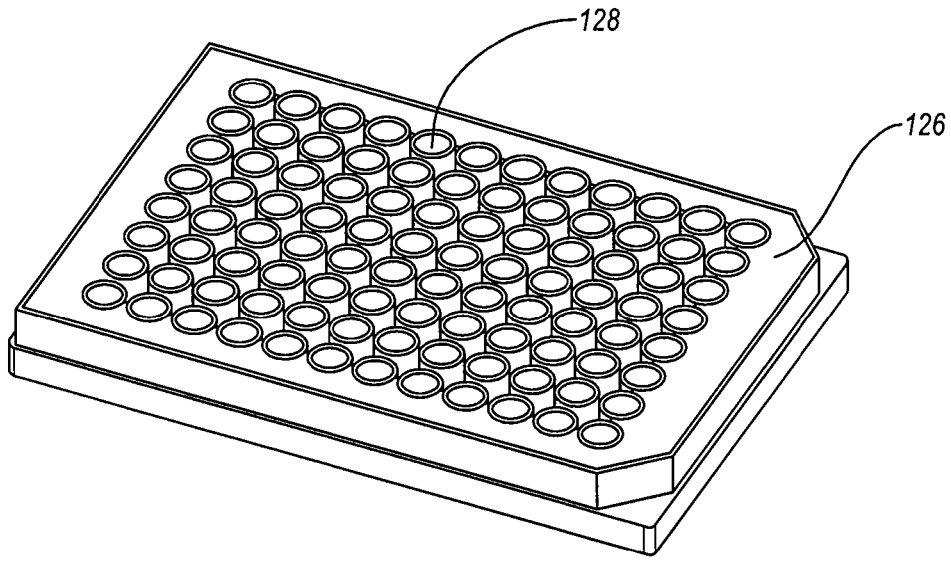
FIG. 3 is a perspective view of a 96-well plate used in various embodiments of the present invention.
FIG. 4 is a spreadsheet showing an exemplary setup for the wells of a 96-well plate.

To accomplish step 122, an assay can be performed on live cells of hepatic origin, such as HepG2 cells or primary hepatocytes from rats or humans to determine whether a compound is hepatotoxic. Other types of cells can also be used. The assay has also been shown to work on fixed cells after cell labeling. The hepatic cells can be grown on multi-well microplates in optimal cell growth media. One such well plate 126 is shown in FIG. 3. Well plate 126 has ninety-six wells 128 arranged in eight rows and twelve columns. Other sized well plates, as are known in the art, can alternatively be used. Well plate 126 can have transparent bottoms to facilitate imaging or other detection methods, if desired. The cells are treated in separate wells 128 for a specific period of time with i) a vehicle (e.g., DMSO or buffer) to be able to provide normalized data, ii) non-hepatotoxic compounds (i.e., negative controls) to determine the thresholds for toxicity prediction and iii) sample compounds where toxicity over a range of concentrations is desired to be known; or known hepatotoxic compounds (used for positive controls).

For example, FIG. 4 illustrates an example plate setup 220 that can be used for well plate 126. In plate setup 220, each cell 222 represents a different well 128 within plate 126. As noted above, in a standard 96-well plate, the wells are arranged in eight rows and twelve columns, which is mirrored in plate setup 220. According to the example setup 220, each well plate includes samples of two separate compounds of interest (denoted "Drug 1" and "Drug 2" in FIG. 4) along with a non-hepatotoxic compound (denoted by "Negative Drug" in FIG. 4).

To take into account sample variations, a plurality of samples of each compound corresponding to different concentrations can be positioned within separate wells. For example, in the exemplary plate setup 220, wells A1, A2, and A3 correspond to three separate samples of Drug 1 at a concentration of 0.75 CMax and wells H7, H8, and H9 correspond to three separate samples of Negative Drug at a concentration of 100 CMax. If desired, the number of samples can be reduced if the sample variation across the plate is low.

Wells are also associated with vehicle control samples (denoted "Control (Vehicle)" in FIG. 4). For example, one or more of the wells (e.g., well "Ref" on FIG. 4) can be used to measure the optimal exposure time for each assay target. Other wells can be used to determine the amount of exposure the plate receives. The exposure values from each plate can then allow a normalization to be computed between plates, as is known in the art. Control (vehicle) samples can be made either in serial dilutes or in a fixed vehicle concentration (e.g., 1% DMSO). It is appreciated that plate setup 220 is exemplary only; other plate setups can alternatively be used.

In the experimental data disclosed below, the hepatic cells were treated with drugs for 24 hours, but other drug treatment times can alternatively be used.

Many of the embodiments disclosed herein simultaneous monitor the responses of multiple cellular targets over a range of compound concentrations. To be able to monitor and analyze the cellular responses to a compound over a range of compound concentrations, the cells are treated with different concentrations of the compound in the microplates so that a range of cellular dose responses for each cellular target is obtained for the compound. For example, in the exemplary plate setup 220 of FIG. 4, each compound has samples corresponding to a range of concentrations between 0.75 CMax and 100 CMax. Of course, other ranges can also be used.

Many cellular targets exhibit toxic responses at different doses for different compounds. For example, as noted above a compound may show its toxicity at an intermediate concentration but not at a higher concentration. Furthermore, the concentration of a drug in blood and in organs after medication is not always the same in different patients and the pharmacokinetics and pharmacodynamics of each compound may differ by individuals. In these conditions, the prediction power of the assay is improved by simultaneously monitoring multiple cellular targets over a range of compound concentrations.

The concentration values of the compounds can range between about 0.5 CMax to about 100 CMax or higher, where CMax is the peak serum concentration of the drug, as is known in the art. Other values can also be used, depending on the compounds tested.

After drug treatment, the hepatic cells are stained with specific fluorescent materials to detect different cellular targets or properties whose changes are associated with cell health, as is known in the art. For example, in the exemplary embodiments discussed herein, as well as in the test data shown, the following five cellular responses are simultaneously monitored:

1. Cell number (i.e., cell loss, cell density)
2. Nuclear DNA content
3. Reduced glutathione (GSH) levels in cells
4. Reactive oxygen species (ROS) levels in cells
5. Mitochondrial membrane potential changes Of course, as noted above, other responses or targets can also be monitored. By way of example and not limitation, the following targets can also be monitored, if desired:

Cell death
Cell proliferation
Cell stress
Cell cycle, DNA damage and repair, and genotoxicity
Cell morphology and shape
Cell motility
Lipids
Calcium
Mitochondrial toxicity.

The additional cellular targets, functions and/or properties (referred to collectively as "targets") can also be included in the assay and simultaneously multiplexed provided that probes detectable by light or fluorescence microscopy or by flow cytometry or other detection systems for the targets exist and do not interfere with the probes for the other targets also being assayed in the cell. An alternative, although less powerful way of looking at additional targets, can be to investigate the targets in a separate set of cells treated to the same compound dose-response format, and combine the results with the targets assayed in the initial set of cells.

Specific fluorescent probes can be used to monitor the five cellular properties discussed above, as is known in the art. The cell staining procedure can be extensively optimized to ensure the proper staining of different cellular targets. Although these cellular targets and properties are monitored for the exemplary embodiments discussed herein, other cellular properties, functions or targets can also be monitored for other cytotoxicity assessments by using similar fluorescent probes as discussed above.

The fluorescently labeled cells can be detected by manual microscopy or by using a fluorescence imaging system, such as, e.g., imaging system 102 (FIG. 1). However, conducting the assay using manual microscopy would be laborious in assaying a range of concentrations for each compound. An automated high-content imaging system provides an effective option to automatically detect and quantify the targets accurately with great speed, enabling the analysis of multiple compounds, doses and conditions. Images of the cells can be acquired in distinct, different colors to detect the different fluorescently labeled cellular targets, and then stored and analyzed using image analysis programs. Furthermore, the imaging can be done simultaneously for all concentrations of a compound, yielding more accurate results. Therefore, an automated imaging system is preferred and was used during testing. The fluorescently labeled cells can alternatively be detected by flow cytometry.

Once imaging has been performed, automated image processing algorithms as are known in the art can be used in the imaging system to determine the measurements in the cell images. For example, the following measurements can be performed as indicated:

Cell loss can be calculated by measuring the number of cells in the image.

Nuclear DNA content can be monitored by measuring the integrated fluorescence intensity of the DNA probe in the nuclear area of each cell with DNA staining Reduced glutathione level can be measured by integrating the fluorescence intensity in the cytoplasmic area of each cell by a cell permeable fluorescent indicator for reduced glutathione.

Reactive oxygen species (ROS) level can be quantified by integrating the fluorescence intensity in the nuclear area of each cell that results from a fluorescent ROS dye staining Mitochondrial membrane potential change can be detected with a probe that is sensitive to mitochondrial membrane potential change, and by measuring the integrated fluorescence intensity difference of this probe between the nuclear and cytoplasmic regions.

Because an imaging system can spatially resolve different regions of an imaged cell, multiple targets can be imaged simultaneously even if the fluorescent probes corresponding to each target have the same emission color when the locations and/or actions of the probes in the same cell can be spatially separately resolved and quantified. Using this approach, Table 1 illustrates two different embodiments that were successfully used for the assay where five different cellular properties were distinctly detected by either using 4 different colors or 3 different colors, as shown in Table 1. In the data obtained and discussed herein, Embodiment 1 of Table 1 was used to obtain the data. Embodiment 1 only uses three colors so that the additional colors that the instrument platform can detect but are currently unused can be utilized in the future to simultaneously monitor additional cellular targets.

TABLE 1

Fluorescent Staining Embodiments of Invention

| Cell Property | Cellular region Where Measurement is Made (measurement method) | Embodiment 1 (3 colors) | | Embodiment 2 (4 colors) | |
|---|---|---|---|---|---|
| | | Probe (Vendor) | Color | Probe (Vendor) | Color |
| Cell Number | Nucleus (counting number of nuclei) | Hoechst 33342 (Thermo Scientific) | Blue | Vibrant Ruby Red (Life Technologies) | Red |
| DNA Content | Nucleus (integrated intensity) | Hoechst 33342 (Thermo Scientific) | Blue | Vibrant Ruby Red (Life Technologies) | Red |
| Reduced Glutathione | Cytoplasm (integrated intensity) | Monochlorobimane (Thermo Scientific) | Blue | Monochlorobimane (Thermo Scientific) | Blue |
| Reactive Oxygen Species | Cell (integrated intensity) | ROS dye (Thermo Scientific) | Green | CM-2DCFDA (Life Technologies) | Green |
| Mitochondrial Membrane Potential | Cytoplasm & Nucleus (integrated intensity difference between regions) | MitoSensor Orange (Thermo Scientific) | Orange | MitoSensor Orange (Thermo Scientific) | Orange |

To accomplish step 124 of FIG. 2, the quantitative cellular target data obtained from the image analysis of the imaged fluorescent cells performed in step 122 can be used to make a hepatotoxicity prediction having high sensitivity and specificity.

Figure 5:
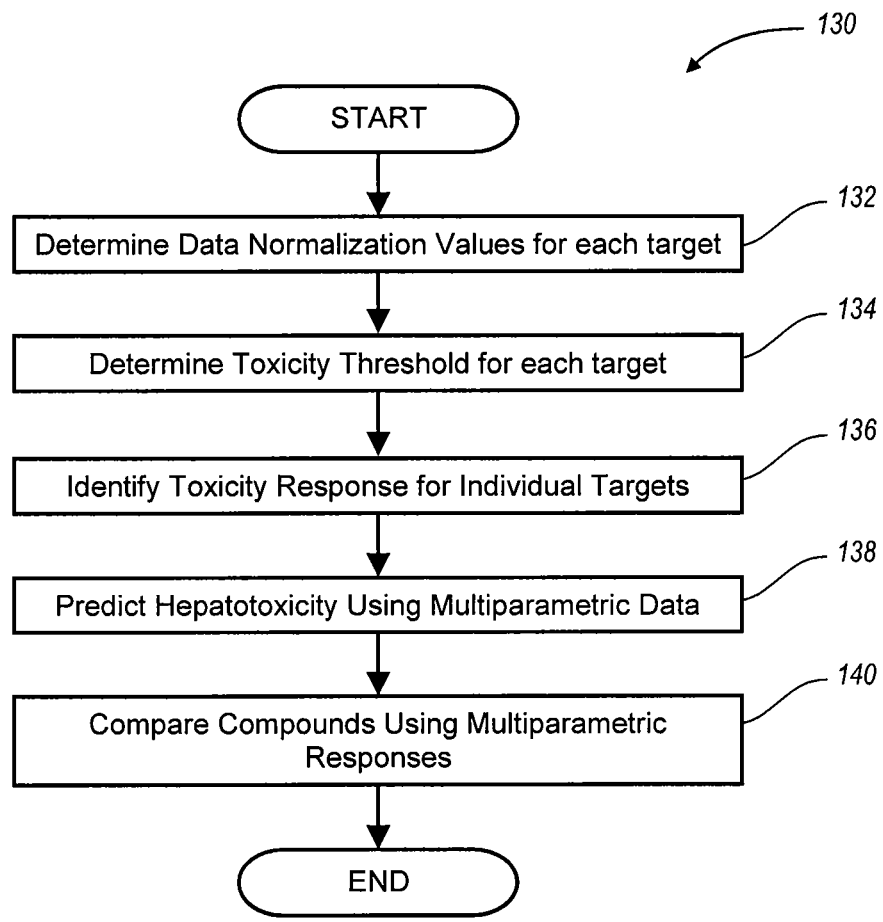
FIG. 5 is a flow diagram illustrating a method for predicting hepatotoxicity of compounds.

FIG. 5 is a flow diagram illustrating one embodiment of a method 130 for accomplishing step 124 of method 120 (FIG. 2) and predicting the hepatotoxicity of compounds. Method 130 includes the following five steps, with the last step being optional:

1. Determining data normalization values (Step 132)
2. Determining toxicity threshold (Step 134)
3. Identifying toxicity response for individual targets (Step 136)
4. Predicting hepatotoxicity using multiparametric data (Step 138)
5. Comparing compounds using multiparametric responses (Step 140)

At step 132, for each cellular target measured, all the responses over all treatment conditions and compound concentrations are normalized based on the values obtained from the vehicle treated hepatic cells. The normalization is performed for each target. This enables comparisons between the different target responses.

For each target measured, the mean from the vehicle control wells $\mu_{vi}$ is computed as follows:

$$\mu_{vi} = (V_{i1} + V_{i2} + \ldots + V_{im})/m \quad \text{Equation (1)}$$

where V is the measured value from the vehicle control wells v for target i and m is the number of measurements taken from the vehicle control wells v for target i.

Using the mean value $\mu_{vi}$ determined for the target, the normalized sample compound response R and negative control response N are computed for each target:

$$R_{CDi} = r_{CDi}/\mu_{vi} \quad \text{Equation (2)}$$

where R and r are the normalized and measured responses respectively for the sample compound C, at dose or concentration D, for target i. That is, the normalized response is equal to the measured response divided by the basal response.

$$N_{Di} = n_{Di}/\mu_{Vi} \quad \text{Equation (3)}$$

where N and n are the normalized and measured responses respectively for the negative control at dose or concentration D, for target i. That is, the normalized response is equal to the measured response divided by the basal response. The negative controls correspond to compounds for which it is known that those compounds are not hepatotoxic at any concentration (i.e., they are non-hepatotoxic compounds).

At step 134, toxicity thresholds for each of the measured cell targets can be determined based on the negative control response once the normalized values have been determined.

First, for each of the cellular targets, a measure of the central tendency of the negative control response distribution can be calculated. Using the central tendency, the statistical dispersion or variation of the negative control response can be used to determine the toxicity thresholds. One manner for doing this is to use the mean to determine the central tendency and the standard deviation to determine the statistical dispersion. Thus, the mean and standard deviation of the normalized response over all the concentrations of all the negative control compounds (i.e., non-hepatotoxic compounds) are calculated. For example, for a five-target assay a mean and standard deviation for each of the five targets can be determined.

The mean over the entire concentration range of all negative control compounds for each target can be calculated as follows:

$$\mu_{Ni} = (N_{D1i} + N_{D2i} + \ldots + N_{Dxi})/x \qquad \text{Equation (4)}$$

where N is the normalized response for the negative control at the particular dose D for target i, determined in accordance with Equation (3), and x is the number of doses or concentrations C for which the normalized value is determined for target i.

The standard deviation over the entire concentration range of all negative control compounds for each target can then be calculated as follows:

$$\sigma_{Ni} = \sqrt{\left(\frac{1}{x}\right)((N_{D1i} - \mu_{Ni})^2 + (N_{D2i} - \mu_{Ni})^2 + \ldots + (N_{Dxi} - \mu_{Ni})^2)} \qquad \text{Equation (5)}$$

Second, the toxicity threshold values for each target can be determined by using the means values $\mu_{Ni}$ determined above. The toxicity threshold of the target is set as the mean $\mu_{Ni}$ plus and minus a coefficient multiplied by the standard deviation $\sigma_{Ni}$. In equation form:

$$\text{Toxicity Threshold}_i = \mu_{Ni} \pm (K_i \times \sigma_{Ni}) \qquad \text{Equation (6)}$$

where $K_i$ is the coefficient with which to multiply the standard deviation for target i.

The coefficient $K_i$ is chosen such that all the normalized values from the non-hepatotoxic compounds are defined to be between the threshold values; however, a coefficient value larger than the calculated value can be used as a threshold value if desired. A proper negative control should not exhibit dramatic changes over the dose range since minimal response (i.e., no toxicity) should occur, and thus should be within the threshold values.

The above equation yields two toxicity thresholds for each measured target:

$$\text{Upper Toxicity Threshold}_i = \mu_{Ni} + (K_i \times \sigma_{Ni}) \qquad \text{Equation (7)}$$

$$\text{Lower Toxicity Threshold}_i = \mu_{Ni} - (K_i \times \sigma_{Ni}) \qquad \text{Equation (8)}$$

In some embodiments one threshold alone can be used, e.g., where it makes sense biologically for specific targets. For example, since an indicator of toxicity is a loss of cells, only the lower toxicity threshold might be used for that target; since cell proliferation and cell number increase may not usually be an indicator of toxicity, an upper toxicity threshold may not need to be determined. As another example, although an increase of intracellular ROS levels are generally considered to be indicators of toxicity, a decrease of intracellular ROS levels are generally not considered such; thus a lower toxicity threshold may not need to be determined for ROS. For other targets (e.g., mitochondrial membrane potential changes or DNA content) it may be desirable to determine both the upper and lower toxicity thresholds.

Figure 6A:
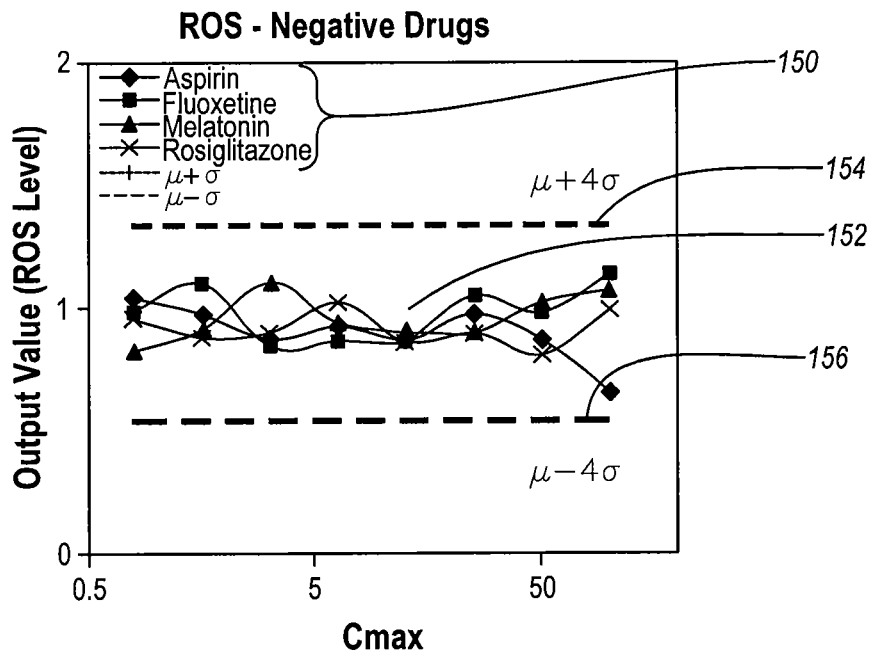
FIGS. 6A and 6B are graphs respectively illustrating an example of how threshold values can be determined and used to determine hepatotoxicity.
Figure 6B:
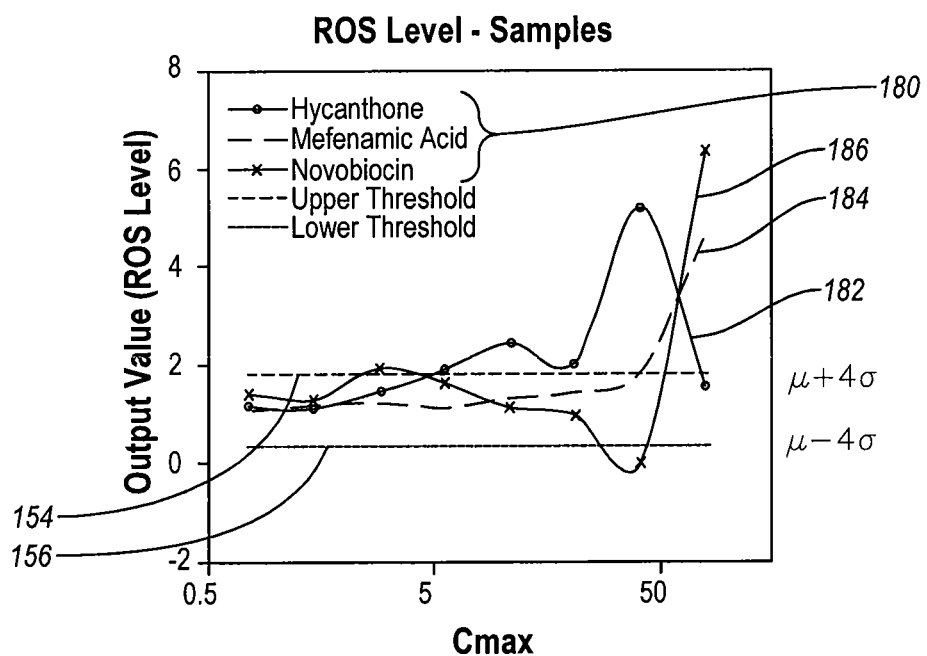

An example of determining and applying thresholds to predict compound toxicity for a particular target is shown in FIGS. 6A and 6B. In FIG. 6A, four non-hepatotoxic drugs (Aspirin, Fluoxetine, Melatonin, and Rosiglitazone) 150 were evaluated over a range of concentrations (up to 100 CMax). The target i being evaluated was the normalized ROS response. The mean $\mu$ and standard deviation $\sigma$ were computed for all four compounds over the full concentration range and a coefficient $K_i = 4$ was selected to give a minimal toxicity threshold so that the responses 152 of all four negative compounds were between the upper and lower thresholds values across all of the concentrations, as computed using Equation 6 above. As a result, for this example, Equation 6 becomes:

$$\text{Toxicity Threshold} = \mu \pm (4 \times \sigma)$$

where $\mu$ is the mean of the normalized non-hepatotoxic compound values and $\sigma$ is the standard deviation of the normalized non-hepatotoxic compound values. The dashed lines 154 and 156 of FIG. 6A respectively represent the upper and lower toxicity threshold values. Note that as shown in FIG. 6A, the responses 152 of all four negative compounds lie between upper and lower threshold values 154 and 156 along the entire range of concentrations. As noted above, the lower toxicity threshold value 156 may be omitted for targets, such as ROS, for which the lower threshold value is not considered indicative of toxicity.

It is appreciated that using the mean and standard deviation, discussed above, to respectively determine the central tendency and the statistical dispersion is only one manner of doing so. Other measures can alternatively be used. For example, the central tendency can also be measured by determining the median, mode, weighted mean, geometric mean, harmonic mean, and midrange, as is known by one having skill in the art of statistics. In similar manner, the statistical dispersion can also be measured by using average absolute deviation, mean absolute deviation, distance standard deviation, interquartile range, mean difference and median absolute deviation, as is known by one having skill in the art of statistics. Other measures of central tendency or variation or statistical dispersion can also be used.

At step 136 of FIG. 5, the toxicity response for each target of each sample compound is evaluated over the full concentration range of the compound using the toxicity thresholds determined in step 134. If the target's normalized response for a particular compound is beyond the toxicity thresholds anywhere over the concentration range, the compound can be flagged as being toxic for that particular target.

Thus, the sample compound can be flagged as toxic for target i if at any dose D, i) the response is above the upper toxicity threshold (i.e., $R_{CDi} > \mu_{Ni} + K_i \times \sigma_{Ni}$) or ii), the response is below the lower toxicity threshold (i.e., $R_{CDi} < \mu_{Ni} - K_i \times \sigma_{Ni}$). Otherwise, the compound is considered non-hepatotoxic.

Figure 7:
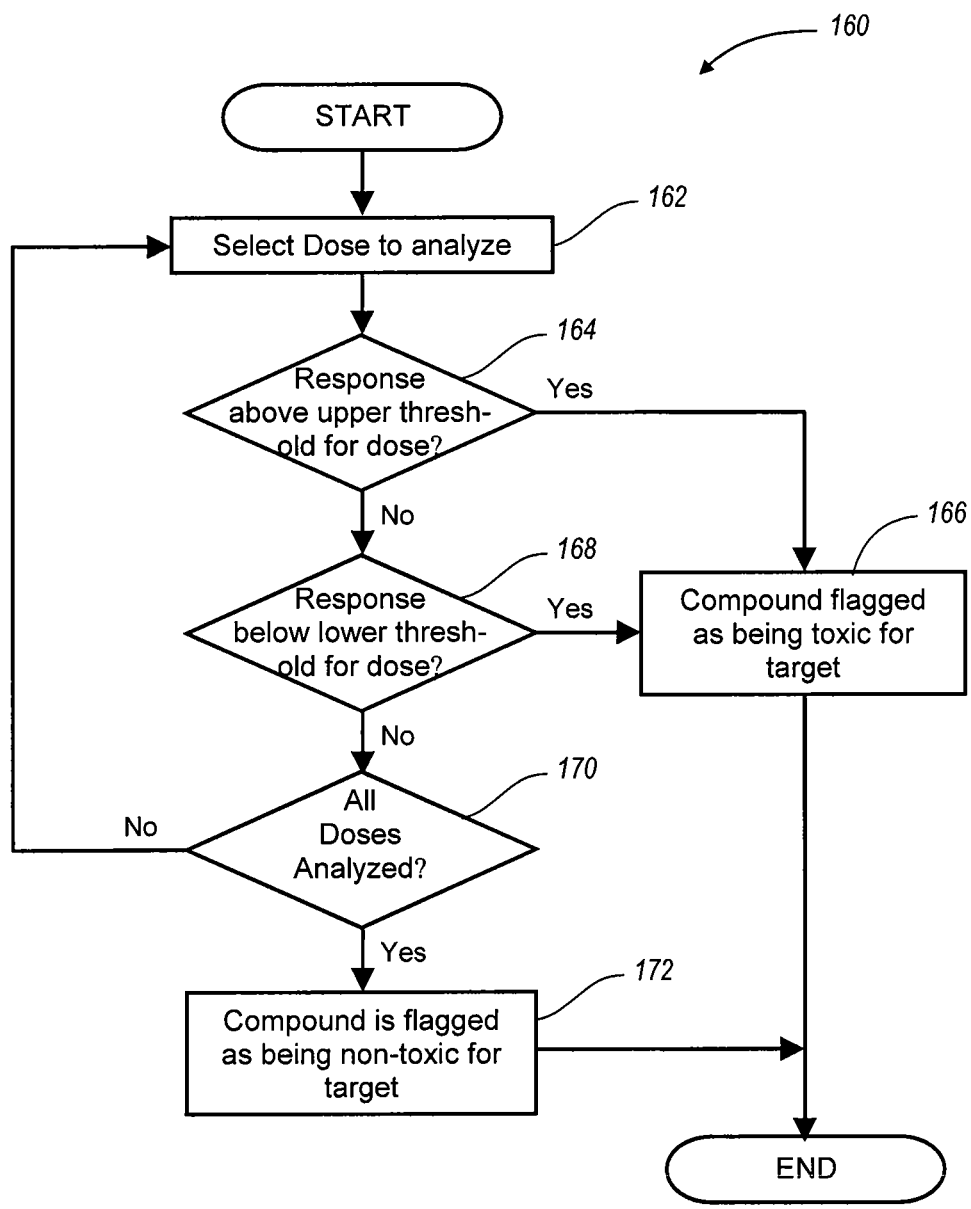
FIG. 7 is a flow diagram illustrating a method for determining the toxicity of a particular target using upper and lower threshold values.

FIG. 7 illustrates an exemplary method 160 of flagging a compound. In step 162, a dose or concentration amount is first selected. In step 164, the compound response corresponding to the selected concentration and to the particular target is compared to the upper toxicity threshold for that target. If the response is greater than the upper toxicity threshold, the compound is flagged as being toxic for the particular target (step 166). Otherwise, In step 168, the compound response is compared to the lower toxicity threshold for that target. If the response is less than than the lower toxicity threshold, the compound is likewise flagged as being toxic for the particular target (step 166). Once the compound has been flagged as being toxic for the particular target at any concentration, the method ends. Otherwise, another dose is selected at step 162 and steps 164 and 168 are repeated. At step 170, if all of the doses have been analyzed, the compound is flagged as being non-toxic for the particular target (step 172) and the method ends. As noted above, the upper toxicity threshold or the lower toxicity threshold can be omitted from the calculation and method 160 revised accordingly, if desired.

Returning to the example discussed above, FIG. 6B shows the toxicity thresholds 154 and 156 determined as shown in FIG. 6A being applied to a normalized ROS response over the same concentration range for three known hepatotoxic drugs (Hycanthone, Mefenamic acid, and Novobiocin) 180. As illustrated, the response values 182, 184, 186 corresponding respectively to Hycanthone, Mefenamic acid, and Novobiocin have ROS response values greater than upper threshold 154 somewhere in the concentration range. As such, all three are flagged as being toxic compounds for the ROS response. As noted above, for ROS, the upper threshold may be all that is needed. Note that the responses for Novobiocin and Hycanthone were not unidirectional and the response for Mefenamic Acid did not follow a classic sigmoidal dose-response curve. As a result, calculating the $EC_{50}$ concentration for all three compounds, as is commonly done in conventional methods, would have been difficult at best and lead to erroneous toxicity determinations at worst. The difficulty in compound toxicity measurement because of non-unidirectional response and/or because of incorrect $EC_{50}/IC_{50}$ calculation from a dose-response curve are avoided by establishing toxicity thresholds based on the negative controls and by flagging a compound as toxic only if its response goes beyond the determined thresholds at any concentration.

In step 138 of FIG. 5, a hepatotoxicity prediction is made based on the results of the toxicity responses for each target in step 136. Since different cellular targets exhibit toxic responses at different concentrations or doses for different compounds, the exemplary assay methods monitor all the different targets for each compound over an extensive concentration range. If a compound is flagged as toxic for any of the targets, then the compound can be predicted to be toxic, as illustrated in method 190 shown in FIG. 8.

Figure 8:
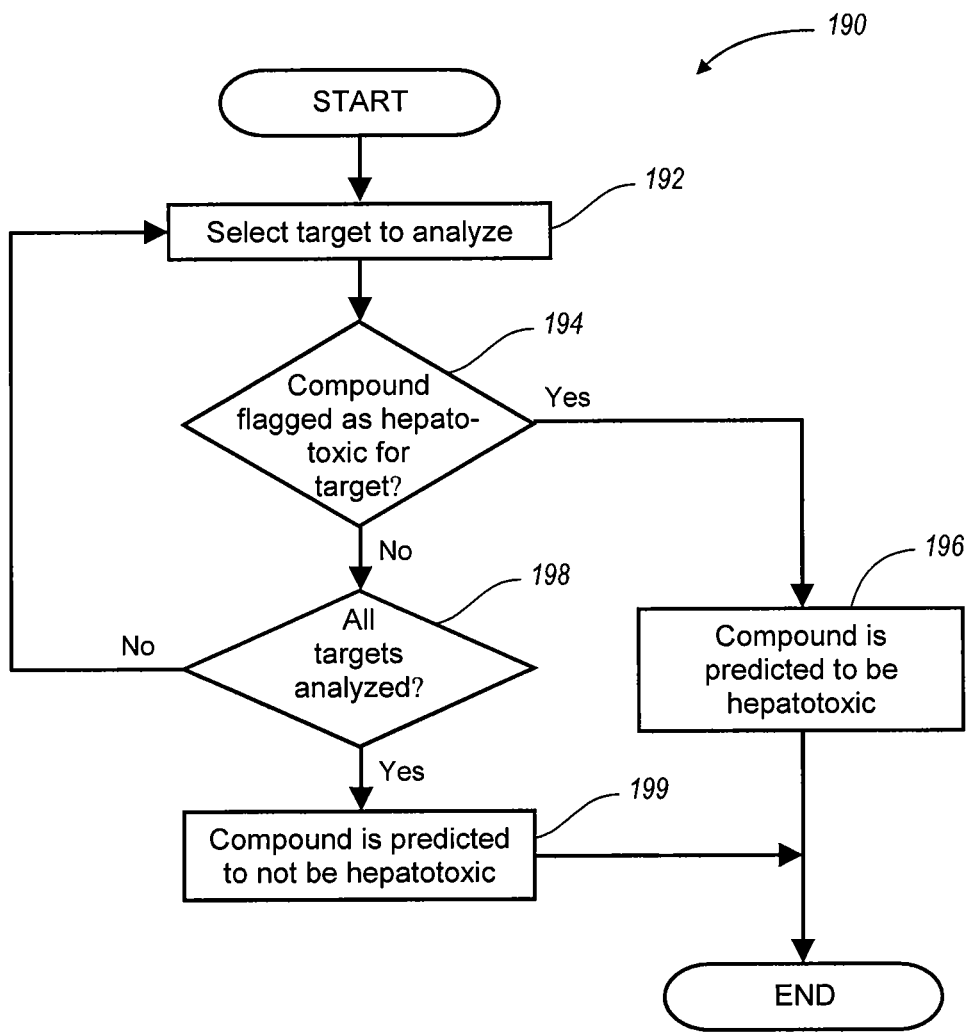
FIG. 8 is a flow diagram illustrating a method for predicting the hepatotoxicity of a compound.

FIG. 8 illustrates an exemplary method 190 of predicting the hepatotoxicity of a compound based on the flagging done in step 136. In step 192, a particular target is selected to be analyzed for the particular compound. If the compound is flagged as being toxic for the particular target (step 194), then the compound is predicted to be hepatotoxic (step 196). Otherwise, another target is selected at step 192 and step 194 is repeated. At step 198, if all of the targets have been analyzed for the particular compound, the compound is predicted as being non-hepatotoxic for the particular target (step 199). Once the compound has been predicted to be hepatotoxic or non-hepatotoxic, the method ends.

Practically, the hepatotoxicity prediction can be achieved by establishing a decision table where the individual determination (i.e., toxic or non-toxic) for each compound and for each target is noted, and then a Boolean OR function can be applied over all the targets for each compound; that is, if any one of the targets is flagged toxic for that compound, then the compound is predicted to be toxic.

FIG. 9 shows an example of an assay decision table 200 according to one embodiment in which methods 160 and 190 were carried out for each compound and target on an experiment performed on rat primary hepatocytes with seventeen compounds (four negative control compounds 202 and thirteen compounds 204 that are known to be hepatotoxic). Five targets 206 were tested. Using methods 160 and 190 discussed above, table 200 displays the results. For each target flagged as being toxic for a particular compound, the corresponding cell in table 200 contains a "+". Otherwise the cell contains a "-". As can be seen, for all of the known hepatotoxic compounds 204, at least one of the target cells corresponding to each compound contains a "+" thereby signifying that the compounds were all flagged as being toxic. In contrast, for all of the known non-hepatotoxic compounds 202, each of the corresponding target cells corresponding to the compounds contains a "-", thereby signifying that the compounds were not flagged as being toxic. Thus, all of the known hepatotoxic compounds were correctly predicted to be hepatotoxic and all of the negative controls were correctly predicted to be non-hepatotoxic. As such, the experiment had no false positives or false negatives, and thus had 100% specificity and 100% sensitivity.

At step 140 of FIG. 5, when a collection of compounds are assessed for toxicity, one may wish to compare and rank the different compounds. The ranking schemes discussed herein are derived from target responses in the assay methods presented herein and are intended to be used as a guide by scientists in the study of the assayed compounds. These ranks may or may not correlate exactly with the true toxicity of the compounds, which can only be determined from in vivo (animal or human) studies. However, by providing the ranking from the in vitro assay, it may help provide insight into the potential true toxicity of the compounds. Thus, the ranking does not mean to suggest that the compound is necessarily truly more toxic than a lesser ranked one, but the potential that this may be the case and should be verified in in vivo determinations. Since the assay can be a multiparametric assay, a multiparametric toxicity index can be calculated to compare compounds. Two exemplary manners of comparing compounds based on the multiparametric responses are given herein according to embodiments of the present invention. They are:

1. Ranking by individual target toxicity; and
2. Ranking by properties of the multidimensional vector.

Other manners of compound comparison can also be used.

To rank by individual target toxicity, the number of targets that are flagged for each compound as toxic can be used to rank the compound's toxicity, with the compounds having the greater number of flagged targets being considered more toxic than the compounds having a lesser number of flagged targets. For example, in the assay decision table 200 shown in FIG. 9, the second to last column lists the number of targets per compound that were flagged as being toxic. This corresponds to the number of target cells corresponding to the compound that contain a "+". As shown, all five targets were flagged as being toxic in six compounds (Gemfibrozil, Hycanthone, Tetracycline, Ticlopidine, Cyproheptadine, Novobiocin); thus, those compounds are given the highest rank for toxicity under this approach. Four targets were flagged as being toxic in six other compounds (FCCP, Mefenamic Acid, Trazodone, Phenylbutazone, Dantrolene, Troglitazone); thus those compounds are given the next highest rank in toxicity. Two targets were flagged as being toxic in Nalidixic acid; thus that compound is given the next highest rank in toxicity. Finally, as noted above, the four negative control compounds (Rosiglitazone, Aspirin, Fluoxetine, Melatonin) are given the lowest rank for toxicity as none of the five monitored targets registered a toxic response in any of the five monitored targets at the thresholds levels used.

In the alternative approach, a single quantitative multiparametric indicator for each compound can be calculated and used to determine the toxicity ranking for each compound. The single quantitative multiparametric indicator can be determined for each compound to reflect the overall response from the multiple measured individual toxicity indicators. The multiparametric indicator can be a property of a multi-dimensional vector representing the response from the different monitored cell targets. For example, if five targets are used, then a five-dimensional vector can be determined. One or more multiparametric indices can then be derived from the multi-dimensional vector representing the measured single toxicity indicators. For example, in the exemplary embodiment shown in FIG. 9, two multiparametric indices can be derived from the five-dimensional vector representing the five measured single toxicity indicators. These indices can include a Euclidean Distance determination and an Angle determination. Both of these indices indicate a deviation of the sample compound response vector from the negative control vector.

Figure 10:
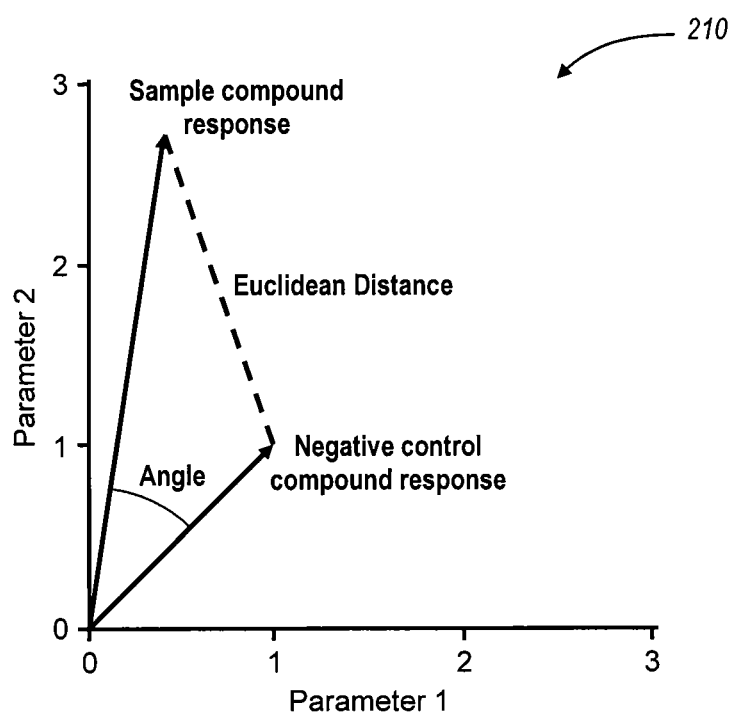
FIG. 10 is a graph showing the Euclidean Distance and Angle of a sample compound with respect to a negative control.

The Euclidean Distance corresponds to the distance of a sample compound's normalized response from the normalized response of the negative control. The Angle corresponds to the angle between the vectors to the normalized negative control and the sample compound's normalized response. To illustrate these concepts, the graph 210 of FIG. 10 shows the multiparametric indices in a 2-dimensional space where only two single parameter toxicity indicators are measured (called Parameter 1 and Parameter 2). This can be extended to a multi-dimensional vector where the different dimensions represent the different cellular targets monitored for a toxicity response. For example, if five different cellular targets are monitored, the Euclidean Distance and Angle of a five-dimensional vector in five-dimensional space can be calculated where the individual axes are the five measured toxicity indicators (e.g., Cell Number, DNA Content, GSH content, Reactive Oxygen Species, Mitochondrial Membrane Potential).

To calculate the Euclidean Distance and Angle for an n-dimensional space, the Sample and Negative compound responses can be represented as the following n-dimensional vectors:

$$S=(s_1, s_2, \ldots s_i) \quad \text{Equation (9)}$$

$$N=(n_1, n_2, \ldots n_i) \quad \text{Equation (10)}$$

where S=Sample compound response vector, N=Negative control compound response vector, i represents the number of cell targets, $s_i$=the sample response for target i, and $n_i$=the negative response for target i.

The Euclidean Distance (ED) can be calculated by applying the Pythagorean Theorem as follows:

$$ED=\sqrt{(n_1-s_1)^2+(n_2-s_2)^2+\ldots+(n_i-s_i)^2} \quad \text{Equation (11)}$$

To calculate the Angle, the inner product (i.e., dot product) of the two vectors can be used because the inner product between the two vectors (e.g., N and S) is defined as the product of dimensions of the two vectors multiplied by the cosine of the Angle between them. Thus:

$$\text{Angle}=\arccos((N \cdot S)/(|N||S|)) \quad \text{Equation (12)}$$

The Euclidean Distance and Angle can be calculated for each monitored concentration of the compound being evaluated. To avoid the issue of these indices varying over the concentration range, the maximum value of the Euclidean Distance and the Angle for each compound over the compound's concentration range can be determined and used to rank the compounds.

Once the Euclidean Distances and Angles of all of the compounds have been calculated, the rankings can be determined. In one embodiment, the Euclidean Distances only are used, with the compounds having the higher Euclidean Distance values being given the higher rankings. Similarly, in another embodiment, the Angles only are used, with the compounds having the higher Angle values being given the higher rankings. In some embodiments the Euclidean Distances and Angles are used together. For example, in one embodiment, separate ranks are determined based on the maximum Euclidean Distances and maximum Angles, as detailed above, and then the mean of the two rankings is determined for each compound to determine the final ranking. In another embodiment, the square root of the sum of the squares of the maximum Euclidean Distance ranks and maximum Angle ranks are used. That is, an overall score is given for each compound as follows:

$$\text{Score}=\sqrt{ED^2+\text{Angle}^2} \quad \text{Equation (13)}$$

The rankings can then be determined by the scores, with the compounds having the higher scores being given the higher rankings. Other ranking schemes can also be used.

Experimental Testing

Test data and results are now given. Table 2 shows drugs that were used during testing and the corresponding drug concentrations corresponding to 1 CMax and 100 CMax values. Note that for FCCP, the CMax values were not known and were therefore set at 1 µM.

TABLE 2

Control Drugs for Hepatotoxicity Prediction Assay

| Compound/Drug | 1 CMax (µg/ml) | 100 CMax (µg/ml) |
|---|---|---|
| a. Hepatotoxicity Negative Drugs | | |
| Aspirin | 0.995 | 99.5 |
| Fluoxetine | 0.015 | 1.5 |
| Melatonin | 0.00557 | 0.557 |
| Rosiglitazone | 0.373 | 37.3 |
| b. Hepatotoxicity Positive Drugs | | |
| Troglitazone | 2.82 | 282 |
| FCCP | (1 µM) | (100 µM) |
| Novobiocin | 62.5 | 6250 |
| Cyroheptadine HCl | 30 | 3000 |
| Phenylbutazone | 150 | 15000 |
| Trazodone HCl | 1.88 | 188 |
| Ticlopidine | 2.13 | 213 |
| Tetracycline | 9.317 | 931.7 |
| Nalidixic Acid | 30 | 3000 |
| Gemfibrozil | 46.4 | 4640 |
| Mefenamic Acid | 6.5 | 650 |
| Dantrolene | 1.24 | 124 |

Various procedures and protocols that can be used during execution of the steps of the inventive methods discussed herein are now given. These procedures and protocols were used during testing. It is appreciated that the procedures and protocols discussed below are exemplary only and that other procedures and protocols can also be used.

A 96-well plate, such as well plate 126 shown in FIG. 3 was used for the assay. The plate set up 220 shown in FIG. 4 was used for the 96-well plate. Other plate sizes and set ups can also be used.

A test protocol was optimized and tested on HepG2 cells (American Type Culture Collection, Product No. HB-8065), rat primary hepatocytes and human primary hepatocytes. However, other immortalized hepatic cells, differentiated hepatocytes from stem cells or primary hepatocytes from different species can also be used.

For routine culture of HepG2 cells, EMEM medium containing the following supplements can be used: 10% fetal bovine serum, 1 mM sodium pyruvate, 1× non-essential amino acids, 100 units/ml penicillin and 100 μg/ml streptomycin (EMEM complete medium).

Cells can be split when they reach 70-90% confluence at a ratio of 1:3-1:5. Cells can be used at a passage number ≤18.

Cells can be harvested by trypsinization, diluted into EMEM complete medium and cell density was determined. Cells are diluted to $2.0 \times 10^5$ cells/ml in EMEM complete medium. 100 μl of the cell suspension are added per well of the 96-well microplate to achieve 20,000 cells/well.

Cells are incubated overnight at 37° C. in 5% $CO_2$ before drug treatment.

For maintenance of rat primary hepatocytes, Williams E medium can be used containing the following supplements: 15 mM HEPES, 1% ITS+, 4 mM Glutamax, 0.1 μM dexamethasone, 50 units/ml penicillin and 50 μg/ml streptomycin (Hepatocyte maintenance medium). The hepatocyte maintenance medium should be used within 3 days after addition of supplements.

It is appreciated that the protocol discussed above may be used with primary hepatocytes (e.g., GIBCO® Fresh Hepatocytes, #RTFY96).

A protocol used for dry solution preparation for a single 96-well plate is now given. The volume can be adjusted accordingly for more than one plate. To prepare Monochlorobimane (mBCL) Stock Solution, 220 μl of DMSO are added to 5 mg of mBCL. mBCL Stock Solution is stable for several months at −20° C. To prepare ROS dye Stock Solution, 20 μl DMSO are added to 1 mg of ROS dye. Appropriate amounts of vials should be used per experiment. One mg of ROS dye contains material for 3-4 microplates (5 μl of ROS Stock Solution is generally used for each 96 well plate). ROS Stock solution can be stored at −20° C. up to two weeks. To prepare Mito dye Stock Solution, 50 μl DMSO are added to 0.4 mg of Mito dye.

Once all of the Stock Solutions have been prepared, appropriate amounts are used. In the present procedure, 10 μl of mBCL Stock Solution, 5 μl of ROS dye Stock Solution, 1 μl of Hoechst 33342, and 4 μl of Mito dye Stock Solution are placed in four separate tubes. The concentrated Stock Solutions should not be mixed without diluting them in culture media to prohibit direct dye-to-dye interaction. Each dye can be diluted with 500 μl of pre-warmed culture medium (37° C.). All the diluted dye solutions are mixed carefully one by one to pre-warmed 8 ml culture media at 37° C.

An example protocol used to culture, treat, and stain the cell cultures is now given.

20,000 cells of HepG2 are placed in 100 μl EMEM complete media per well in a collagen I coated 96-well plate and incubated 16-24 hours at 37° C. in 5% $CO_2$. A plate set up, as discussed above, is used to treat the drugs in the wells of the plate. For example, a plate can be assigned to be treated with the drug in the microplate according to the example set up shown in FIG. 4. For Rat Primary Hepatocytes, the rat primary hepatocytes should be processed preserved in cold preservation media according to the manufacturer's instruction. The rat primary hepatocytes can be washed once with 100 μl hepatocyte maintenance media per well and incubated overnight in a $CO_2$ incubator at 37° C. To reduce variation between wells when using multiple plates, the plates can be spread in the incubator instead of stacked.

Drug stock solution is prepared in sterile DMSO or in an appropriate vehicle. If many compounds need to be tested, a master drug microplate can be made containing 150 μl of twice the concentration of each drug by diluting the drug stock solution in culture medium.

100 μl of 2× concentrated drug solution are added to the corresponding wells and 100 μl of vehicle in culture medium are added to the control wells. Table 2 shows the final drug concentrations.

The plate is incubated for 24 hour at 37° C. in 5% $CO_2$.

The staining solution is prepared and the drug containing media are carefully aspirated from the plate.

100 μl of the warmed Staining Solution are added to each well.

The plate is incubated for 45 minutes at 37° C. Note: To reduce variation between wells when using multiple plates, the plates can be spread apart in the incubator.

The staining solution is carefully aspirated from the plate.

The plate is carefully washed once with 1× HBSS without phenol red at room temperature. Note: The 1× HBSS should not be warmed up at 37° C. The 1× HBSS should be used at room temperature.

The buffer is aspirated and replaced with 100 μl/well of 1× HBSS without phenol red.

The plate is sealed and image acquisition is performed on an imaging system such as a fluorescence microscope, a High-content Screening instrument, or the like using appropriate image analysis software.

An example protocol used to analyze the data received from imaging the cells is now given.

Once multiple images with different targets have been acquired, different intracellular regions in each cell can be assigned by image analysis algorithms as are known in the art. For example, the nuclear region can be masked by DNA staining in the cell and a cytoplasmic region can be assigned as an area outside of the nuclear region, (see, e.g., FIG. 12). Cell number values can be determined by measuring the number of cells in a defined area. DNA intensity value can be determined by integrating fluorescence intensity of the nuclear area with a DNA binding dye. The reduced glutathione level can be measured by integrating fluorescence intensity in the nuclear, cytoplasmic, or whole cell region of each cell with a cell permeable reduced glutathione indicator staining. Reactive oxygen species level can be quantified by integrating fluorescence intensity in the nuclear, cytoplasmic, or whole cell region with a cell permeable reactive oxygen species indicator staining. The change in mitochondrial membrane potential can be measured by calculating the difference of the integrated fluorescence intensity in the nuclear region and in the cytoplasmic region.

Using values obtained by using the above protocols, data normalization as discussed in detail above can be performed.

The control values from vehicle treated cell image analysis can be combined to calculate the mean value of each target. All the data values of each target can then divided by this mean value from the vehicle sample data for each target for normalization.

The normalized data of non-hepatotoxic compounds is determined separately and the mean and the standard deviation values of the combined data over the different doses of non-hepatotoxic compounds can be calculated for each target.

For each target, the minimal coefficient K of the deviation value from the mean of the non-hepatotoxic compound data can be calculated to include all the non-hepatotoxic compounds values between $\mu+K\times\sigma$ and $\mu-K\times\sigma$ values. These values are set respectively as the upper and lower toxicity thresholds for the target. As noted above, for each target both or only one of the thresholds can be used. For example, during testing, both upper and lower threshold values were determined for i) DNA intensity, ii) reduced glutathione level, and iii) mitochondrial membrane potential change; only a lower threshold value was determined for cell loss; and only an upper threshold was determined for reactive oxygen species level.

The normalized values from the hepatotoxic compounds (or compounds of interest) are compared with the threshold value determined above. The compound toxicity is determined by verifying whether the normalized value of the compound is outside the threshold value(s). For example, during testing, i) DNA intensity, ii) reduced glutathione level, and iii) mitochondrial membrane potential change were determined to be toxic if the respective normalized values were greater than the upper threshold value or less than the lower threshold value. Cell loss was determined to be toxic if the normalized value was less than the lower threshold value. Reactive oxygen species level was determined to be toxic if the respective normalized value was greater than the upper threshold value.

Testing Results

The protocols discussed above were employed in conducting an assay on hepatic cells from four different sources:
HepG2 cells—a hepatic carcinoma cell line
Primary rat hepatocytes from a commercial source (Cellz-Direct)
Freshly isolated non-commercial primary rat hepatocytes
Primary human hepatocytes The sixteen compounds listed in Table 2 were used (except for primary human hepatocytes where only fifteen of the sixteen compounds were used, as the Dantrolene had lost potency and thus was not evaluated). The overall results are shown in Table 3. As shown in Table 3, the assay was completely accurate, yielding 100% sensitivity and 100% specificity for all four cell types.

TABLE 3

Assay results from different types or sources of hepatic cells

| Cell Type | Number of Compounds Tested | Sensitivity (True Positive Rate) | Specificity (1 - False Positive Rate) |
| --- | --- | --- | --- |
| HepG2 cells (hepatic carcinoma cell line) | 16 (12 positive 4 negative) | 100% | 100% |
| Commercial 1° rat hepatocytes (from Cellz Direct) | 16 (12 positive 4 negative) | 100% | 100% |
| Freshly isolated 1° rat hepatocytes | 16 (12 positive 4 negative) | 100% | 100% |
| 1° human hepatocytes | 15 (11 positive 4 negative) | 100% | 100% |

Figure 11:
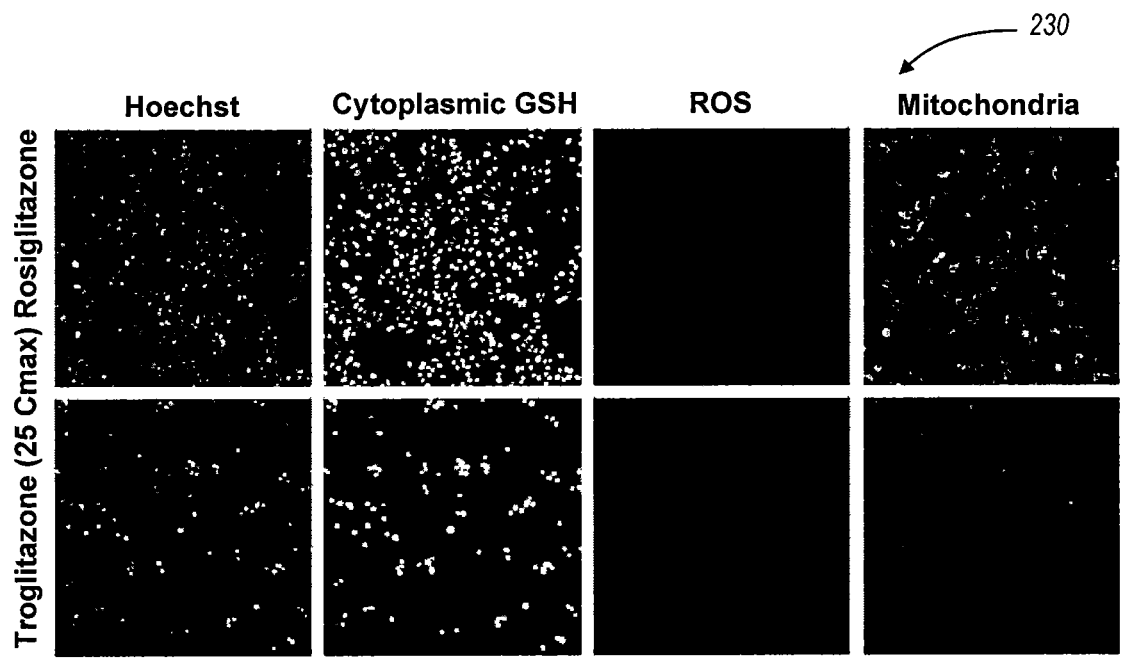
FIG. 11 is a table illustrating photographed images of HepG2 cells, the top and bottom rows respectively showing cells treated with non-hepatotoxic drug Rosiglitazone and hepatotoxic drug Troglitazone, and the columns showing cells stained with specific fluorescent dyes to detect, from left to right, Nuclei, Cellular Glutathione, ROS and Mitochondria.

The cells were treated with a non-hepatotoxic drug, Rosiglitazone (with drug concentration at 100 Cmax) or a hepatotoxic drug, Troglitazone (at 25 Cmax) for 24 hrs. The cells were then stained with specific fluorescent dyes to detect each cellular target. Cell images were then obtained using the ArrayScan VTi Reader manufactured by Cellomics Inc., a subsidiary of Thermo Fisher Scientific Inc. Representative samples 230 of the cell images obtained during the assay are shown in FIG. 11. The cell images show staining of, from left to right, Nuclei, Cellular Glutathione, ROS and Mitochondria in HepG2 cells treated with Rosiglitazone (top row) and Troglitazone (bottom row) using a 10× objective. The images of the cells for the different targets look different for the two drugs; Troglitazone reduces the number of cells and mitochondrial membrane potential but increases reduced glutathione levels in HepG2 cells.

Figure 12:
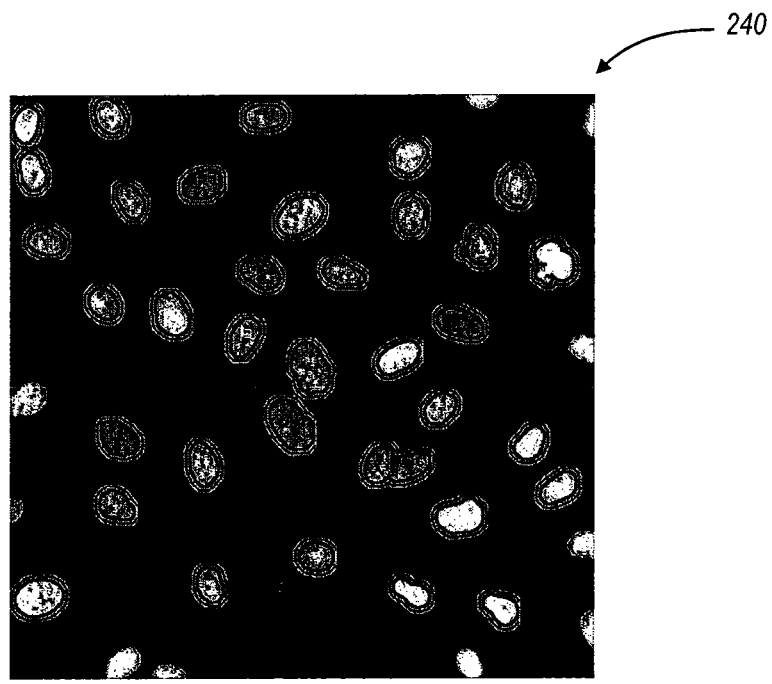
FIG. 12 illustrates a photographed image of Nuclear Staining with DNA dye.

Nuclear DNA was stained with Hoechst 33342 (0.1 μg/ml) and imaged with the ArrayScan VTi HCS Reader. A representative sample 240 of the cell image is shown in FIG. 12. The cell image shows nuclear staining with DNA dye using a 20× objective. The nuclei and cytoplasmic area in the cells were identified using the Compartmental Analysis BioApplication image processing software from Thermo Fisher Scientific, Inc.

Figure 13:
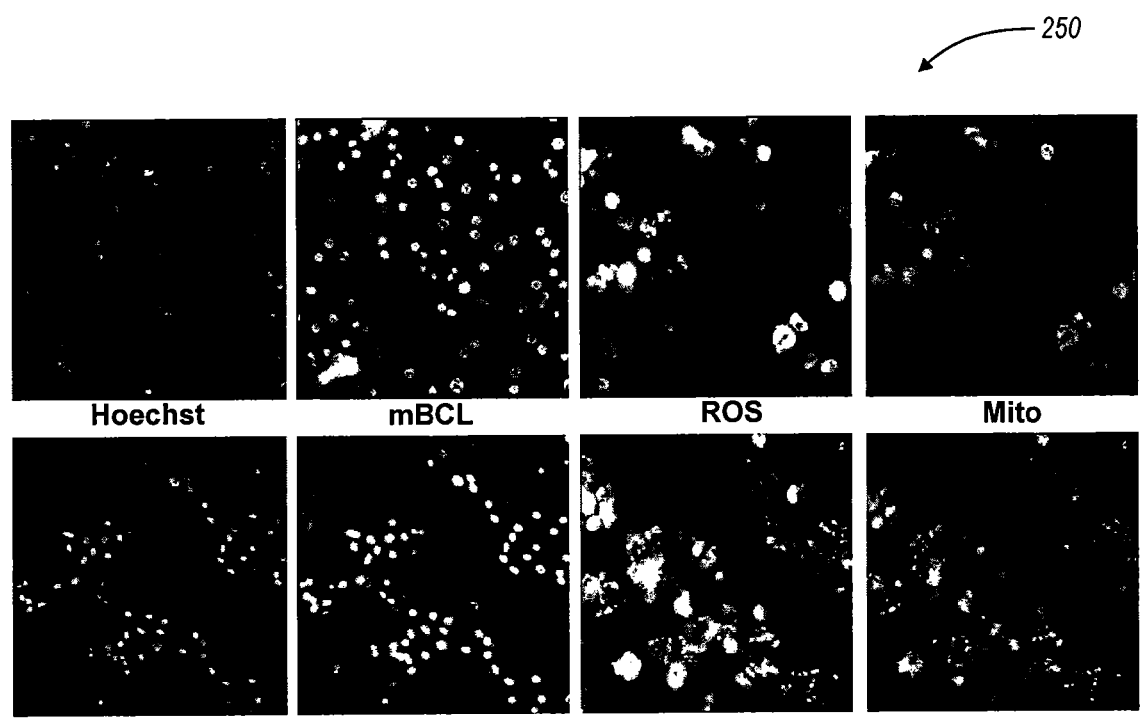
FIG. 13 is a table illustrating photographed images of rat primary hepatocytes, the top and bottom rows respectively showing cells treated with non-hepatotoxic vehicle and hepatotoxic compound FCCP, and the columns showing cells stained with specific fluorescent dyes to detect, from left to right, Nuclei, Cellular Glutathione, ROS and Mitochondria.

The rat primary hepatocytes were treated with vehicle (1% DMSO) or the hepatotoxic compound FCCP (at 100 μM) and then stained with specific fluorescent dyes to detect cellular targets. Cell images were then obtained using the Thermo Scientific ArrayScan VTi Reader. Representative samples 250 of the cell images are shown in FIG. 13, which shows the rat primary hepatocytes using a 20× objective after being treated and stained. The images show DMSO-treated cells (top row) and FCCP-treated cells (bottom row) stained with (from left to right) Nuclei, Cellular Glutathione, ROS and Mitochondria.

The images were analyzed, as discussed above, to produce the data shown on FIG. 9. A prediction of the compound hepatotoxicity on rat primary hepatocytes was generated, based on the results shown in FIG. 9. Four non-hepatotoxic compounds and thirteen hepatotoxic compounds were tested on rat primary hepatocytes. After 24 hours of drug incubation, the hepatocytes were stained and imaged on a Thermo Scientific ToxInsight HCS reader. The data for each target were normalized and analyzed based on the threshold calculated from the non-hepatotoxic compounds in the manner discussed above. If the normalized value for a target went outside the threshold value(s) for a particular compound, that target is shown as positive (+) for the particular compound. In contrast, if the normalized value for the target is in the threshold range, the target is shown as negative (−) for the compound. If any of the targets for a particular compound is positive for toxicity (i.e., has a "+" in the corresponding cell of FIG. 9), the compound is predicted to be hepatotoxic. Thus, thirteen of the seventeen compounds are predicted to be hepatotoxic in the test represented by FIG. 9. As can be seen by FIG. 9, the assay correctly predicted all the hepatotoxic compounds as being hepatotoxic and all the non-hepatotoxic compounds as not being hepatotoxic.

Figure 14:
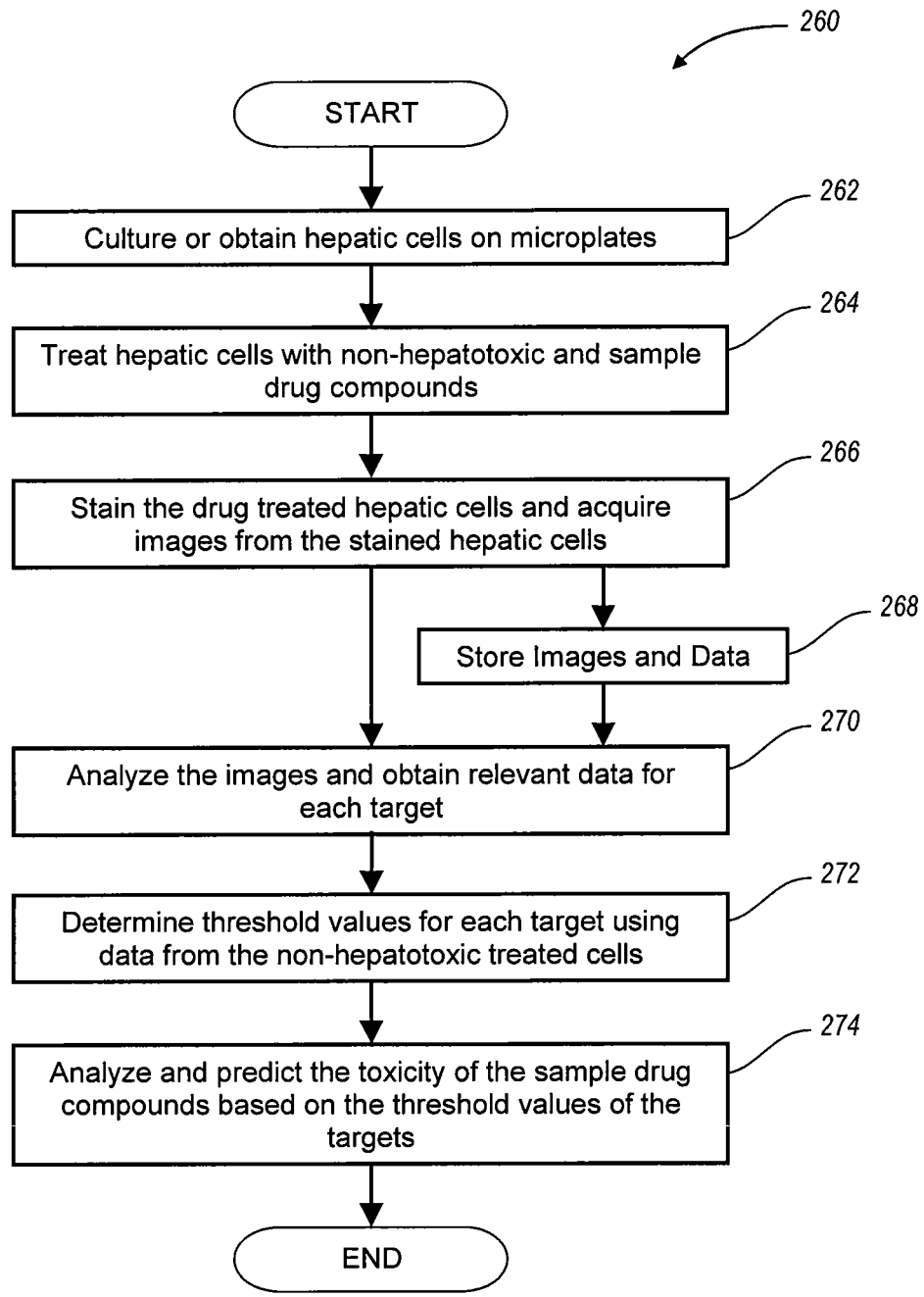
FIG. 14 is a flow diagram showing an alternative method for determining the hepatotoxicity of a compound

FIG. 14 illustrates a flow diagram of an alternative embodiment of a method 260 for determining the hepatotoxicity of a compound. The method can be performed using the exemplary system 100 (FIG. 1) or some other system. In step 262, hepatic cells are obtained or cultured within the wells or other containers of a microplate. In step 264, the hepatic cells of some of the wells are treated with non-hepatotoxic compounds and of other wells are treated with sample compounds for which the hepatotoxicity is not known. For each sample compound, a range of concentrations can be used so that different wells have different concentrations of the sample compound. Similarly, for each non-hepatotoxic compound, a range of concentrations can be used so that different wells have different concentrations of the non-hepatotoxic compound. In step 266 the treated hepatic cells are stained and images acquired based on the targets that are being used. The imaging of the cells can be done using a high-content imaging system, such as imaging system 102 (FIG. 1), as is known in the art. In step 268, the acquired images and related data are stored. The images and data can be stored within the imaging system or an external computing device, such as external computing device 112 (FIG. 1). In step 270, the images are analyzed and relevant data are obtained therefrom. For each compound, images for all of the concentrations can be analyzed. In step 272, threshold values for each target are determined from the data obtained from the range of concentrations of the non-hepatotoxic compounds, as discussed above. In step 274, the compound toxicity of the sample compounds is analyzed and predicted based on the threshold values determined in step 272, as discussed above.

Several publications have shown that a high-content imaging approach can predict compound hepatotoxicity and cytotoxicity with high sensitivity and specificity. Since a toxic insult can affect many cellular properties, this multiparametric cell-based imaging approach is more predictive than other in vitro methods because it simultaneously monitors multiple indicators of cell health to be able to detect a toxicity response, and does so in the proper biological environment of intact cells.

One of the benefits of various embodiments of the present invention is that toxicity variations in different compound concentrations and non-standard cellular responses can be robustly managed upon compound treatment. This can be accomplished as follows:

- assay targets labeled by a simple and optimized fluorescent labeling procedure with specific fluorescent materials
- cells subjected to one of three different types of treatment conditions: cells treated with a vehicle, non-hepatotoxic compounds (i.e., negative controls) or sample compounds (compounds being assessed for hepatotoxicity, or known to be hepatotoxic)
- compounds assayed over a range of concentrations
- normalization of all data by the response from the vehicle treated cells (for each target)
- determination of toxicity thresholds for each cellular target from the mean of all negative control responses plus or minus a coefficient multiplied with the standard deviation of all negative control responses, where the criteria for the coefficient is that it is large enough to include the negative controls within the toxicity thresholds
- the sample compound flagged as toxic if the response for any of the monitored cell targets goes beyond the limits set by the toxicity thresholds Additional benefits provided by embodiments of the invention are multiparametric indices based on the overall response vector compared to the negative control vector which enable the ranking and comparison of the different compounds assessed. Examples of such multiparametric indices are the Euclidean Distance and Angle between the two vectors.

Although discussion herein has been directed to determining hepatotoxicity using the methods presented herein, it is appreciated that other types of toxicity can also be predicted using the methods. For example, neurotoxicity, environmental toxicity, renal toxicity, etc can be predicted by imaging and analyzing neuronal cells, skin cells, renal cells, etc. according to the methods presented herein.

The present invention may be embodied in other specific forms without departing from its spirit or essential characteristics. Accordingly, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of predicting hepatotoxicity of a compound, the method comprising:
    imaging cells of hepatic origin positioned within a plurality of containers to obtain imaged cellular targets, each container being treated with a different concentration of the compound, the imaging being performed using a quantitative high-content cell imaging system;
    quantitatively measuring the imaged cellular targets to detect changes in multiple cellular targets associated with cytotoxicity of the compound; and
    analyzing measurements obtained from the measured imaged cellular targets over a range of compound concentrations, comprising:
        determining data normalization values for each cellular target, comprising:
            determining a mean target value from measurements of vehicle control wells associated with the cellular target;
            determining normalized target response values for the compound at each compound concentration by dividing a measured response of the compound at the corresponding compound concentration by the mean target value; and
            determining normalized target response values for a negative control at each compound concentration by dividing the measured target response of the negative control at the corresponding compound concentration by the mean target value;
        determining toxicity thresholds for each cellular target;
        identifying the toxicity response for each cellular target; and
        predicting hepatotoxicity of the compound using multiparametric data.

2. The method of predicting hepatotoxicity of a compound as recited in claim 1, wherein determining toxicity thresholds for each cellular target comprises:
    determining a second mean target value from measurements of all negative control compounds over the range of compound concentrations associated with the cellular target;
    determining a standard deviation for the target;
    determining an upper toxicity threshold value and a lower toxicity threshold value based on the second mean target value and the standard deviation so that all normalized target values from measured non-hepatotoxic compounds are between the upper and lower threshold values.

3. The method of predicting hepatotoxicity of a compound as recited in claim 2, wherein identifying the toxicity response for each cellular target comprises:
    comparing the normalized target response values of the compound with the upper and lower threshold values with respect to the cellular target over the range of compound concentrations and if any of the normalized target response values are greater than the upper threshold value or less than the lower threshold value, the compound is flagged as being toxic for the particular target, otherwise, the compound is not flagged as being toxic for the particular target.

4. The method of predicting hepatotoxicity of a compound as recited in claim 3, wherein predicting hepatotoxicity of the compound using multiparametric data comprises:
analyzing the toxicity responses of the compound for all of the targets, and if the compound is flagged as being toxic for any target, the compound is predicted to be toxic, otherwise, the compound is predicted to be nontoxic.

5. A computer system programmed to perform the method recited in claim 1.

6. A non-transitory computer readable storage medium having stored thereon computer-executable instructions that, when executed, cause the method recited in claim 1 to be performed.

7. A method of predicting hepatotoxicity of a plurality of compounds, the method comprising:
for each compound:
imaging cells of hepatic origin positioned within a plurality of containers to obtain imaged cellular targets, each container being treated with a different concentration of the compound, the imaging being performed using a quantitative high-content cell imaging system;
quantitatively measuring the imaged cellular targets to detect changes in multiple cellular targets associated with cytotoxicity of the compound; analyzing measurements obtained from the measured imaged cellular targets over a range of compound concentrations, comprising:
determining data normalization values for each cellular target with respect to the particular compound;
determining toxicity thresholds for each cellular target with respect to the particular compound;
identifying the toxicity response for each cellular target with respect to the particular compound; and
predicting hepatotoxicity of the particular compound using multiparametric data; and
ranking the compounds with respect to each other using multiparametric responses, comprising:
determining a single indicator for each compound based on results of the plurality of targets for the compound, comprising generating a multidimensional vector to determine the Euclidean distance and angle of the vector with respect to a negative control sample; and
ranking the compounds based on the single indicators for each compound.

8. A computer system programmed to perform the method recited in claim 7.

9. A non-transitory computer readable storage medium having stored thereon computer-executable instructions that, when executed, cause the method recited in claim 7 to be performed.

10. The method of predicting hepatotoxicity of a plurality of compounds as recited in claim 7, wherein for each compound, Euclidean distances and angles are calculated over the range of compound concentrations and the maximum value of the Euclidean distance and angle are used to rank the compounds.

11. The method of predicting hepatotoxicity of a plurality of compounds as recited in claim 7, wherein the single indicator for each compound is the Euclidean distance determined for the compound and the compounds are ranked based solely on the Euclidean distances of the compounds such that compounds having higher Euclidean distance values are given higher rankings.

12. The method of predicting hepatotoxicity of a plurality of compounds as recited in claim 7, wherein the single indicator for each compound is the angle determined for the compound and the compounds are ranked based solely on the angles of the compounds such that compounds having higher angle values are given higher rankings.

13. The method of predicting hepatotoxicity of a plurality of compounds as recited in claim 7, wherein determining the single indicator for each compound further comprises:
determining a first preliminary ranking of the compounds based solely on the determined Euclidean distances of the compounds;
determining a second preliminary ranking of the compounds based solely on the determined angles of the compounds; and
determining a mean value of the first and second preliminary ranking for each compound, the mean value being used as the single indicator for the compound.

14. The method of predicting hepatotoxicity of a plurality of compounds as recited in claim 7, wherein determining the single indicator for each compound further comprises:
determining a first preliminary ranking of the compounds based solely on the determined Euclidean distances of the compounds;
determining a second preliminary ranking of the compounds based solely on the determined angles of the compounds; and
determining a score for each compound, the score being used as the single indicator for the compound, the score being determined using the following equation:

$$\text{Score} = \sqrt{ED^2 + \text{Angle}^2}$$

where:
ED is the first preliminary ranking of the compound; and
Angle is the second preliminary ranking of the compound.

* * * * *